(12) United States Patent
    Badruddin et al.

(10) Patent No.: US 11,883,032 B2
(45) Date of Patent: Jan. 30, 2024

(54) SYSTEM FOR AND METHOD OF TREATING ANEURYSMS

(71) Applicant: Galaxy Therapeutics Inc., Milpitas, CA (US)

(72) Inventors: Aamir Badruddin, Bolingbrook, IL (US); Edgard Luiz Ramos Pereira, Boca Raton, FL (US); Thomas J. Wolfe, Shorewood, WI (US); Osama O. Zaidat, Lambertville, MI (US)

(73) Assignee: Galaxy Therapeutics, Inc., Milpitas, CA (US)

( * ) Notice: Subject to any disclaimer, the term of this patent is extended or adjusted under 35 U.S.C. 154(b) by 434 days.

(21) Appl. No.: 17/112,229

(22) Filed: Dec. 4, 2020

(65) Prior Publication Data

US 2021/0169496 A1    Jun. 10, 2021

Related U.S. Application Data

(63) Continuation of application No. 15/984,644, filed on May 21, 2018, now Pat. No. 10,856,879, which is a
(Continued)

(51) Int. Cl.
    *A61F 2/958*   (2013.01)
    *A61B 17/12*   (2006.01)
    (Continued)

(52) U.S. Cl.
    CPC .. *A61B 17/12113* (2013.01); *A61B 17/12172* (2013.01); *A61B 17/12177* (2013.01);
    (Continued)

(58) Field of Classification Search
    CPC .............. A61B 17/12; A61B 17/12113; A61B 17/12172; A61B 17/12177; A61F 2/00;
    (Continued)

(56) References Cited

U.S. PATENT DOCUMENTS

| 5,935,148 A | 8/1999 | Villar et al. |
| 6,093,199 A | 7/2000 | Brown et al. |

(Continued)

FOREIGN PATENT DOCUMENTS

| CN | 101489492 | 7/2009 |
| CN | 102871700 B | 4/2015 |

(Continued)

OTHER PUBLICATIONS

Shapiro, M., Raz, E., Becske, T., Nelson, P., "Variable Porosity of the Pipeline Embolization Device in Straight and Curved Vessels: A Guide for Optimal Deployment Strategy", Original Research Interventional, Sep. 26, 2013, 6 pages, 10.3174/ajnr.A3742, American Society of Neuroradiology, Oak Brook, USA.

(Continued)

*Primary Examiner* — Vi X Nguyen
(74) *Attorney, Agent, or Firm* — BLAIR WALKER IP SERVICES, LLC

(57) ABSTRACT

An apparatus for treating an aneurysm in a blood vessel includes a wire to be advanced within a tube and an occlusion element disposed on the wire. The occlusion element includes a cover and an inner anchoring member. The occlusion element is configured to fit within the tube and slide out of an opening at distal end of the tube in response to movement of the wire. The cover is configured to expand to an expanded configuration when advanced into the aneurysm, wherein the cover comprises a diameter that is greater than the diameter of a neck portion of the aneurysm and is configured such that a first portion of the cover contacts an interior surface of the aneurysm and a second portion covers the neck portion of the aneurysm. The inner anchoring member extends from the cover portion and is configured to contact the interior surface of the aneurysm.

20 Claims, 10 Drawing Sheets

Related U.S. Application Data continuation of application No. 15/675,255, filed on Aug. 11, 2017, now Pat. No. 9,980,733, which is a continuation of application No. PCT/US2016/019135, filed on Feb. 23, 2016.

(60) Provisional application No. 62/120,456, filed on Feb. 25, 2015.

(51) Int. Cl.
    *A61F 2/86*         (2013.01)
    *A61F 2/06*         (2013.01)

(52) U.S. Cl.
    CPC ............ *A61F 2/86* (2013.01); *A61B 17/1214* (2013.01); *A61B 17/12118* (2013.01); *A61B 2017/1205* (2013.01); *A61F 2002/068* (2013.01); *A61F 2210/0014* (2013.01); *A61F 2250/0098* (2013.01)

(58) Field of Classification Search
    CPC .... A61F 2/958; A61F 2/86; A61F 2/95; A61F 2/966; A61F 2/07
    See application file for complete search history.

(56) References Cited

U.S. PATENT DOCUMENTS

| | | |
|---|---|---|
| 6,152,144 A | 11/2000 | Lesh |
| 6,391,037 B1 | 5/2002 | Greenhalgh |
| 6,454,780 B1 | 9/2002 | Wallace |
| 6,506,204 B2 | 1/2003 | Mazzochi |
| 6,544,163 B2 | 4/2003 | Wallace et al. |
| 6,613,074 B1 | 9/2003 | Mitelberg et al. |
| 6,936,055 B1 | 8/2005 | Ken et al. |
| 7,128,736 B1 | 10/2006 | Abrams et al. |
| 7,195,636 B2 | 3/2007 | Avellanet et al. |
| 7,229,461 B2 | 6/2007 | Chin et al. |
| 7,410,482 B2 | 8/2008 | Murphy et al. |
| 7,569,066 B2 | 8/2009 | Gerberding et al. |
| 7,749,242 B2 | 7/2010 | Tran et al. |
| 8,142,456 B2 | 3/2012 | Rosqueta et al. |
| 8,388,650 B2 | 3/2013 | Gerberding et al. |
| 8,398,670 B2 | 3/2013 | Amplatz et al. |
| 8,551,132 B2 | 10/2013 | Eskridge et al. |
| 8,597,320 B2 | 12/2013 | Sepetka et al. |
| 8,728,117 B1 | 5/2014 | Janardhan et al. |
| 8,820,207 B2 | 9/2014 | Marchand et al. |
| 8,826,791 B2 | 9/2014 | Thompson et al. |
| 8,940,015 B2 | 1/2015 | Kariniemi |
| 8,998,947 B2 | 4/2015 | Aboytes et al. |
| 9,107,670 B2 | 8/2015 | Hannes et al. |
| 9,113,890 B2 | 8/2015 | Dasnurkar et al. |
| 9,179,899 B2 | 11/2015 | Freudenthal |
| 9,198,668 B2 | 12/2015 | Theobald et al. |
| 9,259,337 B2 | 2/2016 | Cox et al. |
| 9,314,326 B2 | 4/2016 | Wallace et al. |
| 9,510,811 B2 | 12/2016 | Akpinar |
| 9,585,670 B2 | 3/2017 | Hines |
| 9,597,087 B2 | 3/2017 | Marchand et al. |
| 9,629,635 B2 | 4/2017 | Hewitt et al. |
| 9,636,117 B2 | 5/2017 | Bachman et al. |
| 9,855,052 B2 | 1/2018 | Aboytes et al. |
| 9,877,726 B2 | 1/2018 | Liu et al. |
| 9,918,720 B2 | 3/2018 | Marchand et al. |
| 9,980,733 B2 * | 5/2018 | Badruddin ....... A61B 17/12113 |
| 10,111,670 B2 | 10/2018 | Lorenzo et al. |
| 10,123,805 B2 | 11/2018 | Ayres et al. |
| 10,792,045 B2 | 10/2020 | Wang et al. |
| 11,026,694 B2 | 6/2021 | Wang et al. |
| 2003/0176884 A1 | 9/2003 | Berrada et al. |
| 2003/0195553 A1 | 10/2003 | Wallace |
| 2004/0034386 A1 | 2/2004 | Fulton et al. |
| 2004/0044391 A1 | 3/2004 | Porter |
| 2004/0106945 A1 | 6/2004 | Thramann et al. |
| 2004/0172056 A1 | 9/2004 | Guterman et al. |
| 2005/0033409 A1 | 2/2005 | Burke et al. |
| 2005/0107823 A1 | 5/2005 | Leone et al. |
| 2005/0277978 A1 | 12/2005 | Greenhalgh |
| 2006/0064151 A1 | 3/2006 | Guterman et al. |
| 2006/0155323 A1 | 7/2006 | Porter et al. |
| 2006/0206198 A1 | 9/2006 | Churchwell et al. |
| 2007/0088387 A1 | 4/2007 | Eskridge et al. |
| 2007/0173928 A1 | 7/2007 | Morsi |
| 2007/0208376 A1 | 9/2007 | Meng |
| 2007/0225794 A1 | 9/2007 | Thramann et al. |
| 2007/0270902 A1 | 11/2007 | Slazas et al. |
| 2008/0097495 A1 | 4/2008 | Feller, III et al. |
| 2008/0147100 A1 | 6/2008 | Wallace |
| 2008/0281350 A1 | 11/2008 | Sepetka et al. |
| 2008/0319533 A1 | 12/2008 | Lehe |
| 2009/0062841 A1 * | 3/2009 | Amplatz .......... A61B 17/12159 606/200 |
| 2009/0082803 A1 | 3/2009 | Adams et al. |
| 2009/0099647 A1 | 4/2009 | Glimsdale et al. |
| 2009/0264978 A1 | 10/2009 | Dieck et al. |
| 2009/0287291 A1 | 11/2009 | Becking et al. |
| 2009/0318941 A1 | 12/2009 | Sepetka et al. |
| 2010/0179583 A1 | 7/2010 | Carpenter |
| 2011/0046719 A1 | 2/2011 | Frid |
| 2011/0144669 A1 | 6/2011 | Becking et al. |
| 2011/0196413 A1 | 8/2011 | Wallace et al. |
| 2011/0202085 A1 | 8/2011 | Loganathan et al. |
| 2012/0065667 A1 | 3/2012 | Javois et al. |
| 2012/0143317 A1 | 6/2012 | Cam et al. |
| 2012/0245675 A1 | 9/2012 | Molaei et al. |
| 2012/0283768 A1 | 11/2012 | Cox et al. |
| 2012/0303052 A1 | 11/2012 | Connor |
| 2012/0310270 A1 | 12/2012 | Murphy et al. |
| 2012/0330347 A1 | 12/2012 | Becking et al. |
| 2013/0035665 A1 | 2/2013 | Chu et al. |
| 2013/0066357 A1 | 3/2013 | Aboytes et al. |
| 2013/0073026 A1 | 3/2013 | Russo et al. |
| 2013/0190800 A1 | 4/2013 | Murphy et al. |
| 2013/0211495 A1 | 8/2013 | Halden et al. |
| 2014/0005714 A1 | 1/2014 | Quick et al. |
| 2014/0012303 A1 | 1/2014 | Heipl |
| 2014/0052233 A1 | 2/2014 | Cox et al. |
| 2014/0142608 A1 * | 5/2014 | Eskridge .......... A61B 17/12022 606/200 |
| 2014/0172001 A1 | 6/2014 | Becking et al. |
| 2014/0257360 A1 | 9/2014 | Keillor |
| 2014/0343602 A1 | 11/2014 | Cox et al. |
| 2015/0005811 A1 | 1/2015 | Lubock et al. |
| 2015/0133989 A1 | 5/2015 | Lubock et al. |
| 2015/0250628 A1 | 9/2015 | Monstadt et al. |
| 2015/0272589 A1 | 10/2015 | Lorenzo |
| 2015/0313605 A1 | 11/2015 | Griffin |
| 2016/0022445 A1 | 1/2016 | Ruvalcava et al. |
| 2016/0030050 A1 | 2/2016 | Franano et al. |
| 2016/0278749 A1 | 9/2016 | Javois et al. |
| 2016/0317277 A1 | 11/2016 | Carpenter et al. |
| 2017/0095254 A1 | 4/2017 | Hewitt et al. |
| 2017/0156734 A1 | 6/2017 | Griffin |
| 2017/0224350 A1 | 8/2017 | Shimizu et al. |
| 2017/0224355 A1 | 8/2017 | Bowman et al. |
| 2017/0367708 A1 | 12/2017 | Mayer et al. |
| 2018/0140305 A1 | 5/2018 | Connor |
| 2019/0053810 A1 | 2/2019 | Griffin |
| 2019/0110796 A1 | 4/2019 | Jayaraman |
| 2019/0192168 A1 | 6/2019 | Lorenzo |
| 2019/0357914 A1 | 11/2019 | Gorochow et al. |
| 2020/0113576 A1 | 4/2020 | Gorochow et al. |
| 2021/0103667 A1 | 4/2021 | Hewitt et al. |
| 2021/0275184 A1 | 9/2021 | Hewitt et al. |
| 2022/0125567 A1 | 4/2022 | Center et al. |

FOREIGN PATENT DOCUMENTS

| | | |
|---|---|---|
| CN | 103006285 B | 6/2015 |
| DE | 102012016555 A1 | 2/2014 |
| DE | 102013006503 A1 | 7/2014 |
| EP | 2647343 B1 | 7/2017 |
| JP | 2003-190175 | 7/2003 |

(56) References Cited

FOREIGN PATENT DOCUMENTS

| | | |
|---|---|---|
| JP | 2006-509578 | 3/2006 |
| JP | 2009-512515 | 3/2009 |
| WO | WO1999/05977 A1 | 2/1999 |
| WO | WO2002/00139 A1 | 1/2002 |
| WO | WO2007/047851 | 4/2007 |
| WO | WO2009/132045 | 10/2009 |
| WO | WO2015/148821 | 10/2015 |
| WO | WO2017/102804 A1 | 6/2017 |
| WO | WO2017/153603 A1 | 9/2017 |
| WO | WO2017/220400 A1 | 12/2017 |

OTHER PUBLICATIONS

Perez, M., Henkes, H., Bouillot, P., Brina, O., Slater, L., Pereira, V., "Intra-aneurysmal hemodynamics: evaluation of pCONus and pCANvas bifurcation aneurysm devices using DSA optical flow imaging", Journal of NeuroInterventional Surgery, Dec. 23, 2015, 6 pages, 10.1136/neurintsurg-2015-011927, Society of NeuroInterventional Surgery, Fairfax, USA.

Control, etc. http://www.asianjns.org/articles/2012/7/4/images/AsianJNeurosurg_2012_7_4_159_106643_f7.jpg downloaded from internet Apr. 3, 2020.

Cerus https://neuronewsinternational-wpengine.netdna-ssl.com/wp-content/uploads/sites/3/2016/07/Cerus-Endovascular-Contour-300x194.jpg downloaded from internet Apr. 3, 2020.

Contour https://neuronewsinternational-wpengine.netdna-ssl.com/wp-content/uploads/sites/3/2017/06/Contour-e1497957260381-300x194.png downloaded from internet Apr. 3, 2020.

Medtronic https://evtoday.com/images/articles/2017-02/0217-endovascular-fig1.png downloaded from internet Apr. 3, 2020.

International Search Report and Written Opinion, PCT/US2016/019135 dated Jun. 6, 2016, 6 pages.

Extended European Search Report, European App. No. 16756188.5, dated Sep. 26, 2018. 12 pages.

English translation of Office Action and Search Report, Chinese app. No. 201680012003.4, dated Nov. 11, 2019, 5 pages.

\* cited by examiner

SYSTEM FOR AND METHOD OF TREATING ANEURYSMS

CROSS-REFERENCE TO RELATED APPLICATIONS

This application is a continuation of U.S. patent application Ser. No. 15/984,644, filed on May 21, 2018, now U.S. Pat. No. 10,856,879, which is a continuation of U.S. patent application Ser. No. 15/675,255, filed on Aug. 11, 2017, now U.S. Pat. No. 9,980,733, which is a continuation of International Application No. PCT/US2016/019135, filed on Feb. 23, 2016, which claims priority to and the benefit of U.S. Application No. 62/120,456, filed on Feb. 25, 2015, each of which is incorporated herein by reference in its entirety.

BACKGROUND

Aneurysms are abnormal bulging or weakening of a blood vessel, often an artery, and can have many complications. A bulging of the blood vessel can disrupt or put pressure on surrounding tissues. In the brain, this can result in a variety of side effects, such as impaired vision, impaired speech, impaired balance, etc. Further, the aneurysm creates a volume that is not along the main flow path of the blood through the blood vessel. It therefore can serve as a location for blood to become stagnant and, due to swirling eddy currents, can contribute to the formation of a thromboembolism. If the aneurysm ruptures, they can cause severe internal bleeding.

Aneurysms can be treated externally with open surgery. Such procedures typically involve closing off the entrance or "neck" of the aneurysm with a device such as vascular clamp or a ligature. However, such open surgical procedures can be highly invasive and may lead to trauma to the adjacent tissue and other side effects.

Aneurysms can also be treated through endovascular procedures. In one procedure, detachable lengths of wires (e.g., coils) are inserted into the interior volume of the aneurysm using a catheter. The coils are intended to fill the volume of the aneurysm to decrease the flow of blood into the aneurysm, inducing stagnation of flow and stimulate clotting within the aneurysm. In settings of large cerebral aneurysms, filling of the aneurysm with multiple coils can lead to mass effect that may induce brain swelling and be an independent cause for new symptoms. In another procedure, for aneurysms with a relatively large neck, the adjunctive use of stents assists with the retention of the coils within the aneurysm. This approach has a contraindication to being used when treating ruptured aneurysm, due to the need for additional anti-thrombotic medications. In another procedure, the coils are held in the volume of the aneurysm with a temporary balloon that is inflated in the blood vessel. The balloon is deflated and removed once the mass of coils is secured. In still another procedure, a stent device is placed in the artery to promote flow of blood past the aneurysm. This leads to stagnation of the blood within the aneurysm and thrombosis inside the aneurysm volume. However, a side branch of a main artery in which the stent device is placed may become trapped or "jailed", which impedes access to the side branch. In other instances, the side branch can become clotted off, possibly causing a stroke. Additionally, such a procedure generally requires the use additional anti-thrombotic medications, which limits the use of such devices in the setting of treatment of ruptured aneurysms. The stent device is generally formed with a relatively tight weave. While the tight weave increases the effectiveness of the stent device in diverting the blood flow, it also impedes or prevents access to the volume of the aneurysm or the jailed artery. In the event that the aneurysm fails to clot, the obstruction of the aneurysm by the stent device prevents the possibility of placing embolic devices inside the aneurysm. Additional procedures such as the placement of additional stents or open surgery may then be required to treat the residual.

All procedures that involve packing the volume of the aneurysm suffer from several common shortcomings. First, it can take many coils of wire to fill the volume of the aneurysm, which is time consuming and increases the time it takes to complete the procedure. Further, the coils may be compacted over time to occupy a smaller percentage of the total volume of the aneurysm. A great enough compaction of the coils can be considered a recurrence of the aneurysm and may require further treatment.

It would be advantageous to provide an improved system and method of treating an aneurysm.

SUMMARY

One embodiment relates to a catheter for treating an aneurysm in a blood vessel. The catheter includes a tube, a wire disposed within the tube; and an occlusion element. The occlusion element is disposed on the wire. The occlusion element is configured to fit within the tube and slide out of an opening at distal end of the tube in response to movement of the wire within the tube. The occlusion element is configured to expand to have a radius greater than a radius of the tube and cover a neck portion of the aneurysm.

One embodiment relates to a method treating an aneurysm in a blood vessel. The method includes providing a distal portion of a tube to a neck region of the aneurysm, and sliding a wire attached to an occlusion element within the tube so that the occlusion element exits the tube at the neck region. The method also includes separating the occlusion element from the wire after the occlusion element exits the tube.

One embodiment relates to an occlusion system for treating an aneurysm in a blood vessel. The occlusion system includes a wire, and an occlusion element disposed on the wire. The occlusion element is configured to be compressed in a conical shape and expand in a disk or concave shape for covering a neck portion of the aneurysm.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

These and other features, aspects and advantages of the present invention will become apparent from the following description, appended claims, and the accompanying exemplary embodiments shown in the drawings, which are briefly described below.

DETAILED DESCRIPTION

Figure 1:
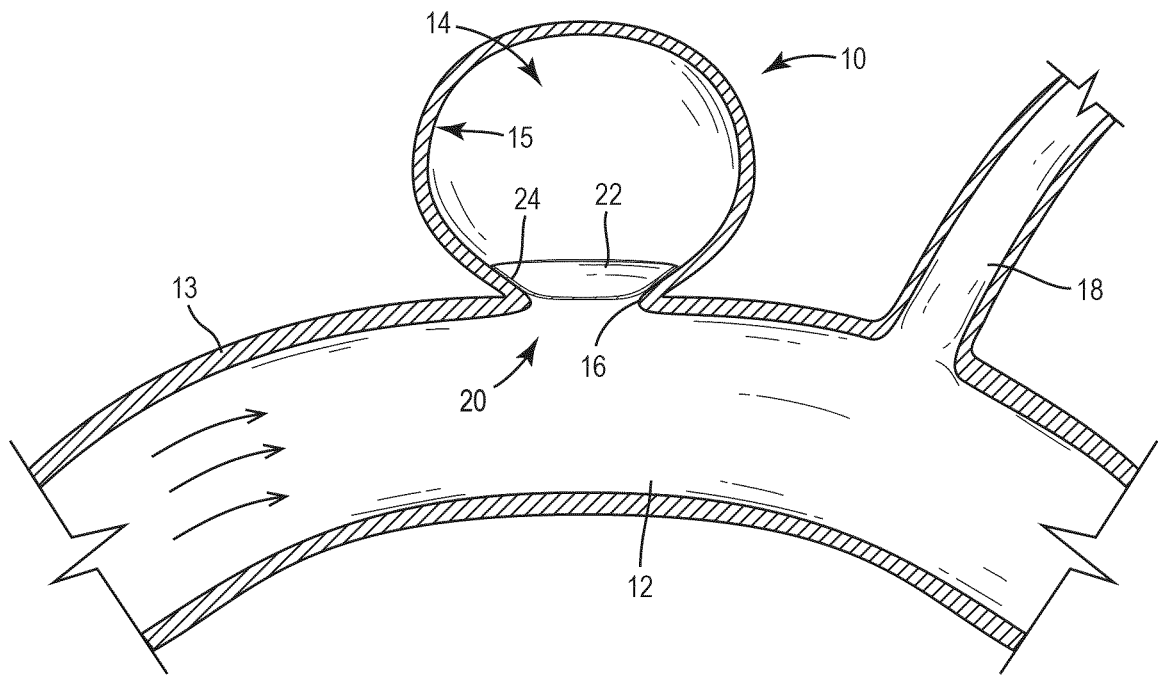
FIG. 1 is a schematic cross-section side view of an aneurysm with an endovascular device configured to occlude the aneurysm, according to an exemplary embodiment.

Referring in general to FIGS. 1-14, an aneurysm occlusion device configured to treat an aneurysm 10 is shown according to several exemplary embodiments. The aneurysm 10 is an outwardly extending bulge in the wall 13 of a blood vessel 12 and has an internal volume 14 that is in fluid communication with the blood vessel 12 through an opening at a neck portion 16. The aneurysm 10 may occur at a portion of the blood vessel 12 at which the wall 13 is weakened by disease or trauma. In one embodiment, the aneurysm 10 may be along an artery, such as a cranial artery (e.g., e.g., basilar artery, middle cerebral artery, etc.). The aneurysm 10, as depicted in the figures is exemplary only and it should be appreciated that the occlusion devices as described herein may be utilized in the treatment of aneurysms of various sizes and locations. For example, the aneurysm 10 may be located between two branches of a blood vessel.

Referring to FIGS. 1-3E, an occlusion device 20 is shown according to one exemplary embodiment disposed in the neck portion 16 of the aneurysm 10 to disrupt or halt the flow of blood flow between the vessel 12 and the internal volume 14 of the aneurysm, thereby reducing the likelihood that the aneurysm 10 will rupture. The occlusion device 20 is configured to be low profile device, minimizing disruptions to surrounding bodies, such as a side branch 18 of the blood vessel 12. The occlusion device 20 may be configured to be biodegradable or bioabsorbable material and may be configured to promote endothelialization.

The occlusion device 20 includes an inner cover 22 (e.g., plate, membrane, etc.) disposed within the internal volume 14 of the aneurysm 10. The inner cover 22 has an outer diameter that is greater than the diameter of the neck portion 16. The inner cover 22 is a thin, flexible, concave body that can be distorted (e.g., collapsed) to be inserted through the neck portion 16 into the internal volume 14 of the aneurysm 10 (e.g., inserted by a catheter) and opened to at least partially occlude the neck portion 16. Concave, as used herein, is meant to describe any body that is contoured to have a hollow or cavity along one side. As shown in FIG. 1, in one exemplary embodiment, the inner cover 22 may be generally dome-shaped. In another embodiment, the inner cover 22 may have another concave shape (e.g., conical) that is disposed in the neck portion 16 and opens into the internal volume 14. In one embodiment, cover 22 can be disk shaped.

The inner cover 22 is formed from a flexible (e.g., soft) biocompatible material that can be collapsed into a microcatheter for endovascular delivery to the aneurysm 10. The flexibility of the inner cover 22 allows it to conform to the shape of the interior surface 15 of the aneurysm 10 and more effectively impeded the flow of blood between the aneurysm 10 and the blood vessel 12. Closely conforming to the shape of the interior surface 15 of the aneurysm 10 also facilitates the adhesion of the inner cover 22 to the tissue of the aneurysm 10 and the formation of new tissue to close off the neck portion 16.

Figure 2:
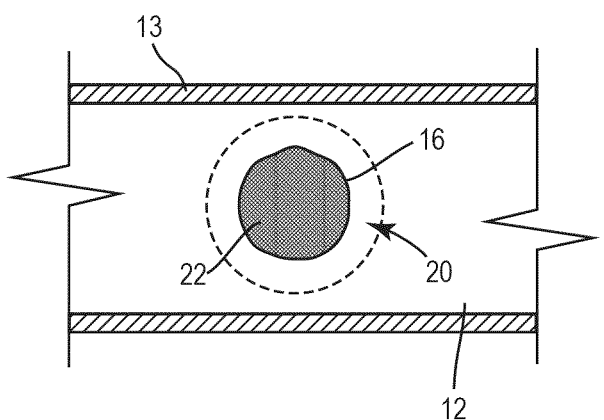
FIG. 2 is schematic cross-sectional bottom view of the aneurysm occlusion device of FIG. 1.

The inner cover 22 may be sized to fit a specific aneurysm 10. As shown in FIGS. 1-2, the inner cover 22 has a diameter that is greater than the diameter of the neck portion 16 such that a peripheral portion 24 of the inner cover 22 contacts the interior surface 15 of the aneurysm 10. The flexibility of the inner cover 22 allows the inner cover 22 to be oversized relative to the size of the neck portion 16 without damaging (e.g., rupturing) the aneurysm 10. For example, an inner cover having a diameter of approximately 5 mm may be utilized to occlude an aneurysm having a neck portion with a diameter of up to 4 mm; an inner cover having a diameter of approximately 8 mm may be utilized to occlude an aneurysm having a neck portion with a diameter of 4-6 mm;

and an inner cover having a diameter of approximately 12 mm may be utilized to occlude an aneurysm having a neck portion with a diameter of 6-10 mm.

In one embodiment, the inner cover 22 may be formed from a biocompatible metal or metal alloy, such as platinum, stainless steel, titanium, a titanium-nickel alloy (e.g., nitinol). For example, the inner cover 22 may be a concave disk formed from sheet-cut nitinol. The nitinol alloy may be configured to undergo a secondary heat setting to form the desired concave shape. According to an exemplary embodiment, the inner cover 22 may have a thickness of less than 100 microns, to achieve a desired flexibility. In another embodiment, the inner cover 22 may be formed as a relatively dense mesh such as 37 micron mesh formed by a plurality of wires or fibers that are coupled together (e.g., welded, soldered, woven, etc.).

In another embodiment, the inner cover 22 may be formed from a biocompatible polymer, such as polytetrafluoroethylene (PTFE), modified polyurethane, silicone or other suitable polymer. In still other exemplary embodiments, the inner cover 22 may be formed from a metal or alloy that is coated with a polymer (e.g., parylene, PTFE, PFE, etc.) to increase lubricity and biocompatibility and to reduce thrombogenicity. The inner cover 22 may be formed as a solid sheet or membrane or may be a relatively dense mesh. In some embodiments, the inner cover 22 may include laser drilled nylon sheeting to provide a matrix for endothelialization, while reducing the bulk of the segment. Another embodiment may involve two photon polymerization, or 3-D printing of a biocompatible material to form the inner cover 22 directly onto the delivery system, or to overlie a skeleton frame which is attached to the delivery system, allowing customization of the final shape of the inner cover 22 at the time of treatment.

Figure 3A:
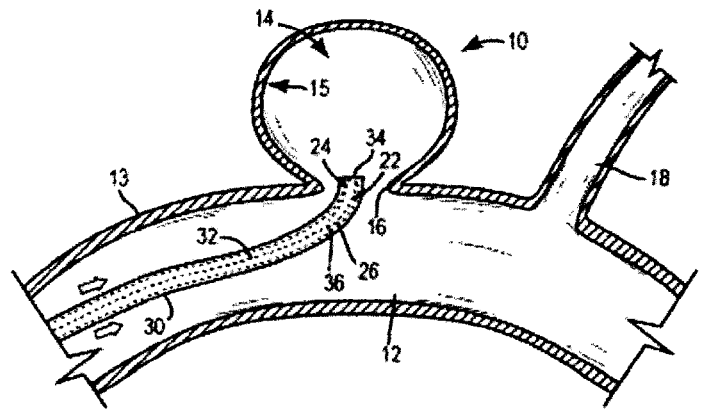
FIGS. 3A-3E are schematic side cross-section views of a catheter deploying the aneurysm occlusion device of FIG. 1, according to an exemplary embodiment.
Figure 3B:
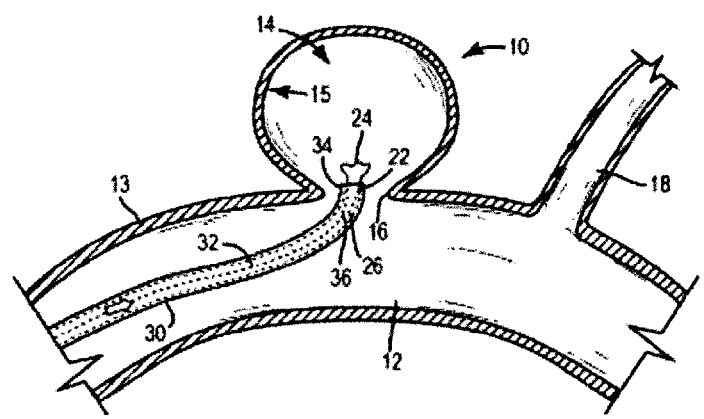

Referring now to FIGS. 3A-3D, the inner cover 22 is showing being deployed with a catheter 30 according to an exemplary embodiment. Referring to FIG. 3A, the catheter 30 including a push wire 32 is advanced through the blood vessel 12 to the location of the aneurysm 10. A distal end 34 of the catheter is advanced through the neck portion 16 and into the internal volume 14 of the aneurysm 10 or to the portion of the blood vessel 12 proximate the neck portion 16. The push wire 32 is positioned within a lumen formed in the catheter 30. The catheter 30 may have a single lumen or the push wire 32 may be positioned within one of several lumens formed within the catheter 30. The inner cover 22 is coupled to a distal end 36 of the push wire 32 and is housed, in a collapsed configuration, within the lumen. In the collapsed configuration, the peripheral portion 24 of the inner cover 22 is upstream (e.g., closer to the distal end 34) compared to a central portion 26 to which the push wire 36 is coupled. Referring to FIG. 3B, the push wire 32 is moved within the lumen relative to the catheter 30 until the inner cover 22 begins to emerge from the end 34 of the catheter 30. The inner cover 22 is configured to expand (e.g., due to the internal spring forces of the inner cover 22) into an expanded configuration within the internal volume 14 as it clears the end 34 of the catheter 30. The push wire 32 may be moved relative to the catheter 30 by holding the catheter 30 stationary while the push wire 32 is advanced (e.g., pushing), by holding the push wire 32 stationary and retracting the catheter 30 (e.g., unsheathing), or by a combination of movements of the catheter 30 and the push wire 32. The inner cover 22 may be partially deployed with the distal end 34 of the catheter 30 positioned within the blood vessel 12 or within the aneurysm 10.

Figure 3C:
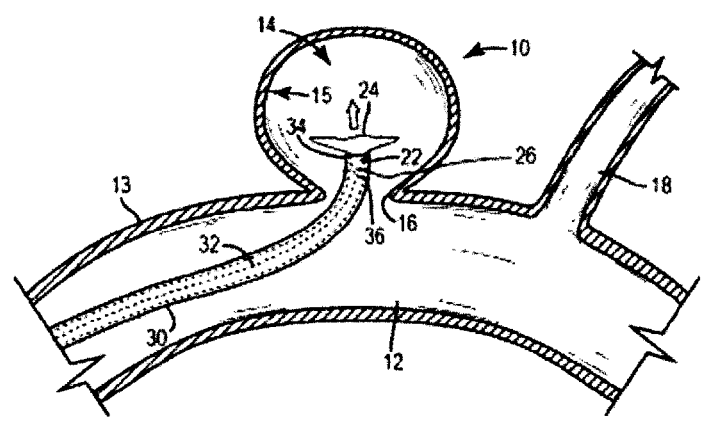
Figure 3D:
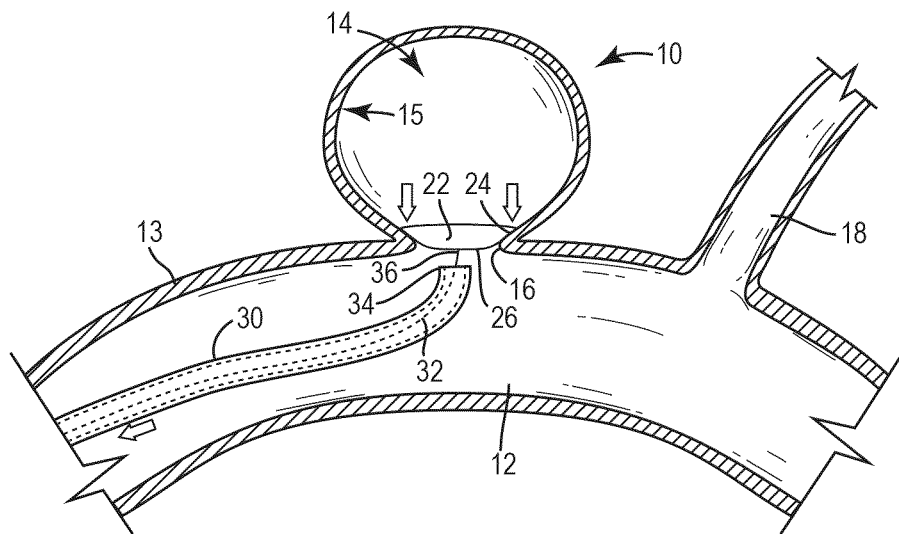
Figure 3E:
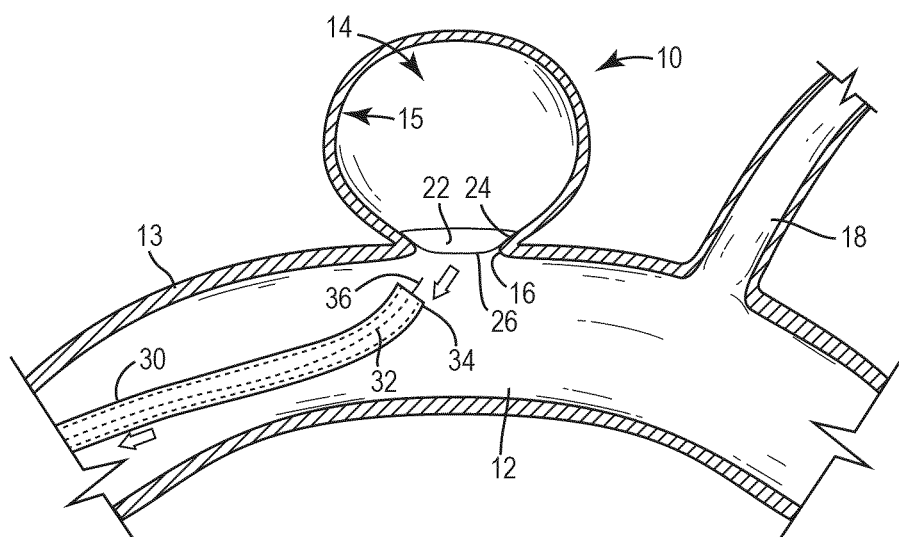

Referring to FIG. 3C, the distal end 34 of the catheter 30 is advanced into the internal volume 14 of the aneurysm 10 before the inner cover 22 is fully deployed from the catheter 30. Referring to FIG. 3D, with the inner cover 22 deployed from the catheter 30, the catheter 30 and/or the push wire 32 is retracted until the inner cover 22 is seated against the interior surface 15 of the aneurysm. Referring to FIG. 3E, the distal end 36 of the push wire 32 is detached from the inner cover 22 such that the catheter 30 and the push wire 32 may be withdrawn from the blood vessel 12 while the inner cover 22 remains in the neck portion 16 of the aneurysm 10. The push wire 32 may be detached from the inner cover 22 by any suitable electrical or mechanical cutting device. Alternatively, the inner cover 22 can be removed by pulling the wire 32 from cover 22 causing cover 22 to engage distal end of tube 30 and be slid off wire 32.

In one embodiment, the inner cover 32 can be formed to be biased toward the open position. In another embodiment, the inner cover 32 can include a mesh supported by rib members or splines radiating outwardly form a center of inner cover 32. The rib members or splines are biased toward an open position in one embodiment. In one embodiment, the rib members and splines operate in an upside down umbrella operation fashion and lock in the fully open position once the fully open position is reached.

Figure 4:
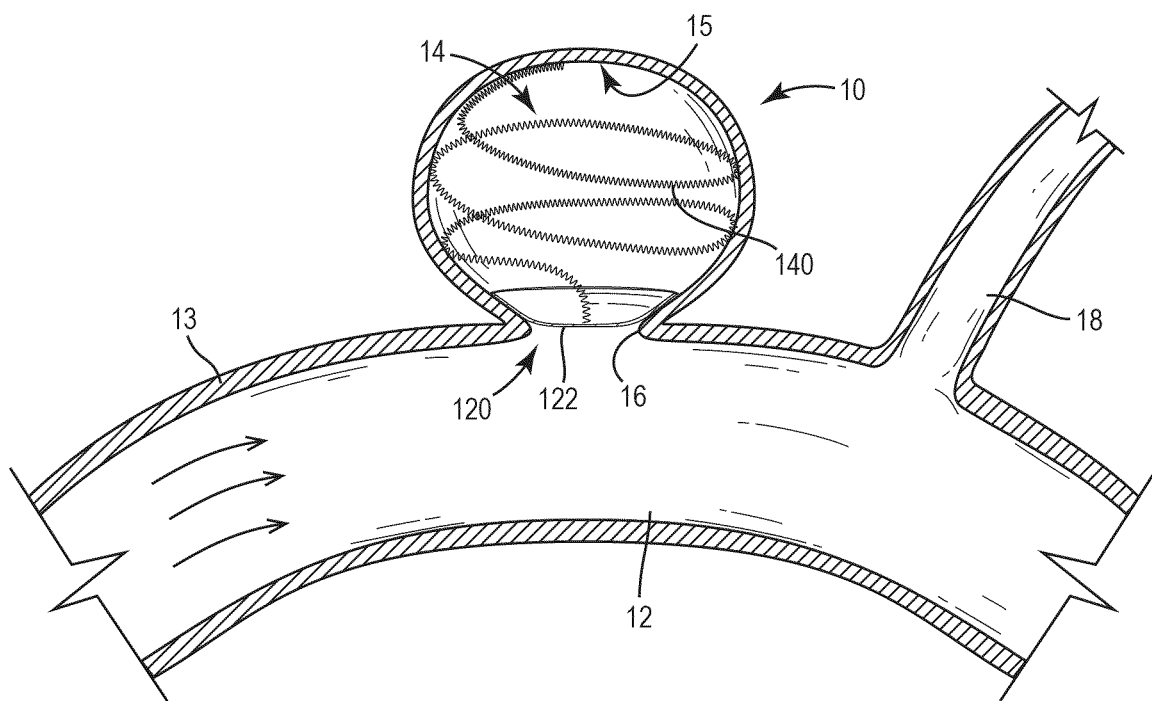
FIG. 4 is a schematic cross-section side view of an aneurysm with an endovascular device configured to occlude the aneurysm, according to another exemplary embodiment.
Figure 5:
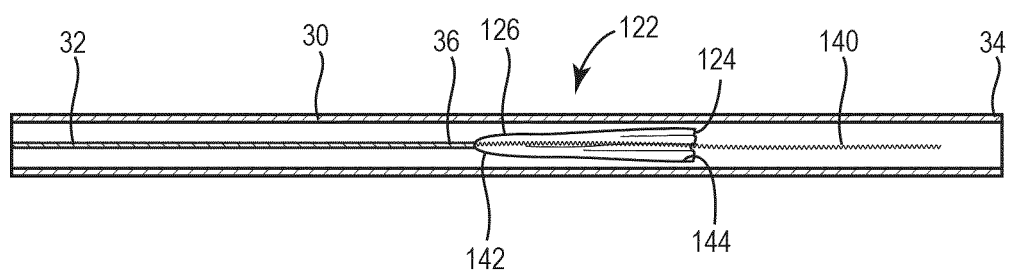
FIG. 5 is a schematic cross-section view of the occlusion device of FIG. 4 inside of a catheter, according to an exemplary embodiment.

Referring now to FIG. 4-5, an occlusion device 120 is shown according to an exemplary embodiment disposed in the neck portion 16 of the aneurysm 10 to disrupt or halt the flow of blood flow between the vessel 12 and the internal volume 14 of the aneurysm, thereby reducing the likelihood that the aneurysm 10 will rupture. The occlusion device 120 is configured to be low profile device, minimizing disruptions to surrounding bodies, such as a side branch 18 of the blood vessel 12. The occlusion device 120 may be configured to be biodegradable or bioabsorbable material and may be configured to promote endothelialization.

The occlusion device 120 includes an inner cover 122 (e.g., plate, membrane, etc.) disposed within the internal volume 14 of the aneurysm 10 and similar to the inner cover 22 described above. The occlusion device 120 further includes an inner anchoring member 140 disposed within the aneurysm 10. The inner anchoring member 140 is configured to anchor the inner cover 122 within the aneurysm 10 in the neck portion 16. The inner anchoring member 140 provides a relatively rigid body that supports the inner cover 122 and reduces the likelihood that the inner cover 122 will be displaced from the neck portion 14 by the fluid pressure of the blood in the blood vessel 12.

According to an exemplary embodiment, the inner anchoring member 140 includes one or more loops of a coil formed from a suitable biocompatible metal or alloy (e.g., platinum, stainless steel, nickel-titanium alloy, etc.). The metal coil may be similar to the coils that are typically utilized in an endovascular coiling procedure. The inner anchoring member 140 is coupled to the inner cover 122 and includes at least one coil that contacts the interior surface 15 of the aneurysm 10. The loops of the inner anchoring member 140 do not fill the entire internal volume 14 or a substantial portion of the internal volume 14. Instead, the inner anchoring member 140 may include only a small number of loops. In one exemplary embodiment, the inner anchoring member 140 may include a single loop of the coil. In another embodiment, the anchoring member 140 includes a large number of loops substantially filing the internal volume 14. The orientation, number, and size of the loops of the inner anchoring member 140 may vary depending on the size and shape of the aneurysm 10.

Referring now to FIG. 5, the inner cover 122 and the inner anchoring member 140 are shown disposed within a catheter 30 according to an exemplary embodiment. The inner cover 122 is coupled to a distal end 36 of the push wire 32 and is housed, in a collapsed configuration, within the lumen of the catheter 30. In the collapsed configuration, the peripheral portion 124 of the inner cover 122 is upstream (e.g., closer to the distal end 34) compared to a central portion 126 to which the push wire 36 is coupled on a first surface 144. The inner anchoring member 140 is coupled to a second surface 146 of the inner cover 122 opposite the first surface 142 and is disposed within the lumen of the catheter 30 upstream of the inner cover 122.

The occlusion device 120 including the inner cover 122 and the inner anchoring member 130 is deployed within the aneurysm 10 similar to the process described above with reference to FIGS. 3A-3E. With the distal end 34 of the catheter 30 positioned proximate to the neck portion 16 of the aneurysm 10, the push wire 32 is moved within the lumen relative to the catheter 30. The push wire is moved to cause the anchoring member 40 to reach the internal volume 14 and coil within the internal volume.

In one embodiment, the push wire 32 has a circular solid cross section and anchoring member 140 has a coiled cross section (e.g., like a telephone cord) to facilitate coiling in the internal volume 14. In one embodiment, the push wire 32 and the anchoring member 140 have a circular solid cross section. In one embodiment, the push wire 32 and anchoring member have a coiled solid cross section.

After coiling of the anchoring member is complete, the inner anchoring member 140 is pushed out of the catheter and into the internal volume 14, where is contacts the interior surface 15 of the aneurysm 10. The push wire 32 is moved further until the inner cover 122 begins to emerge from the end 34 of the catheter 30 to expand into an expanded configuration within the internal volume 14. The catheter 30 and/or the push wire 32 is then retracted until the inner cover 122 is seated against the interior surface 15 of the aneurysm 10 and held in place by the inner anchoring member 140. The distal end 36 of the push wire 32 is detached from the first surface 146 of the inner cover 122 such that the catheter 30 and the push wire 32 may be withdrawn from the blood vessel 12 while the inner cover 22 remains in the neck portion 16 of the aneurysm 10 with the inner anchoring member 140 coupled to the second surface 146.

Figure 6:
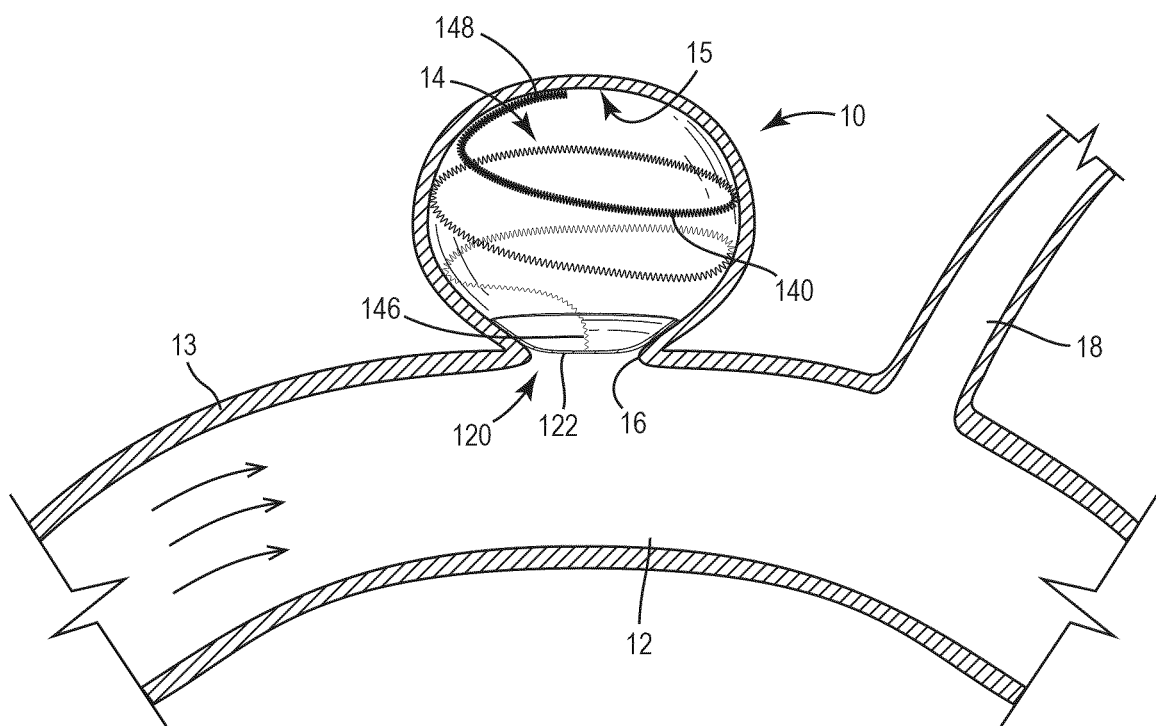
FIG. 6 is a schematic cross-section side view of an aneurysm with an endovascular device configured to occlude the aneurysm, according to another exemplary embodiment.

Referring to FIG. 6, in one exemplary embodiment, the anchoring member 140 may have a variable stiffness. For example, the inner anchoring member 140 may be relatively pliable at a proximal end 146 and relatively stiff at a distal end 148. The relatively stiff distal end 146 may be configured to provide additional support to strengthen the walls of the aneurysm 10. The stiffer portions of the inner anchoring member 140 may be utilized as framing members to create a structure in the internal volume 14 of the aneurysm while the more pliant portions are utilized to fill in the internal volume of the aneurysm and support the inner cover 122. The stiffness of the inner anchoring member 140 may be controlled in a variety of ways, such as by varying the thickness of the coil, the radius of the coil, and/or by varying the material used to form the coil.

The more pliant portions of the inner anchoring member may include a removable sheathe or layer to facilitate the positioning of the stiffer portions of the inner portions of the anchoring member 140 within the aneurysm 10. The sheathe may be removed once the distal end 148 and the stiffer portions of the inner anchoring member 140 are positioned.

In one embodiment, the stiffness of the inner anchoring member 140 may transition smoothly or incrementally along the length of the inner anchoring member 140 between the distal end 148 and the proximal end 146. In other exemplary embodiments, the inner anchoring member 140 may include two or more distinct zones or portions, each with a different stiffness or other characteristic. The inner anchoring member 140 may include markers or other indicators to delineate the transition from one zone to another. In one embodiment, the indicators may be external, such as indicators provided on an outer shaft coupled to the push wire, each of the outer indicators corresponding to the transition from a zone with a first stiffness to a zone with a second stiffness. In another embodiment, the indicators may be internal, such as radiopaque indicators (e.g., a platinum coating) on the inner anchoring member 140 between the zones.

In one embodiment, the anchoring member 140 with a variable stiffness can be utilized without the inner cover 122. In such an embodiment, the anchoring member 140 fills the internal volume 14. In one embodiment, a number of anchoring members 140 can be utilized. In one embodiment, the first employed anchoring member 140 has a varying stiffness (e.g., thickness) that is greater than the varying stiffness (e.g., thickness) of the next employed anchoring member.

Referring now to FIG. 7-10, an occlusion device 220 is shown according to an exemplary embodiment disposed in the neck portion 26 of the aneurysm 20 to disrupt or halt the flow of blood flow between the vessel 22 and the internal volume 24 of the aneurysm 20, thereby reducing the likelihood that the aneurysm 20 will rupture. The occlusion device 220 is configured to be low profile device, minimizing disruptions to surrounding bodies, such as a side branch 28 of the blood vessel 22. The occlusion device 220 may be configured to be biodegradable or bioabsorbable material and may be configured to promote endothelialization.

The occlusion device 220 includes an inner cover 222 (e.g., plate, membrane, etc.) disposed within the internal volume 14 of the aneurysm 10 and similar to the inner cover 22 described above and an inner anchoring member 240 disposed within the aneurysm 10 and similar to the inner anchoring member 140 described above. The inner anchoring member 240 is configured to anchor the inner cover 222 within the aneurysm 20 in the neck portion 16. The occlusion device 220 further includes an outer anchoring member 250 disposed in the within the blood vessel 12 proximate the aneurysm 10. The outer anchoring member 250 provides a relatively rigid body that supports the inner cover 222 and reduces the likelihood that the inner cover 222 will be displaced from the neck portion 14 by the fluid pressure of the blood in the blood vessel 12.

Figure 7:
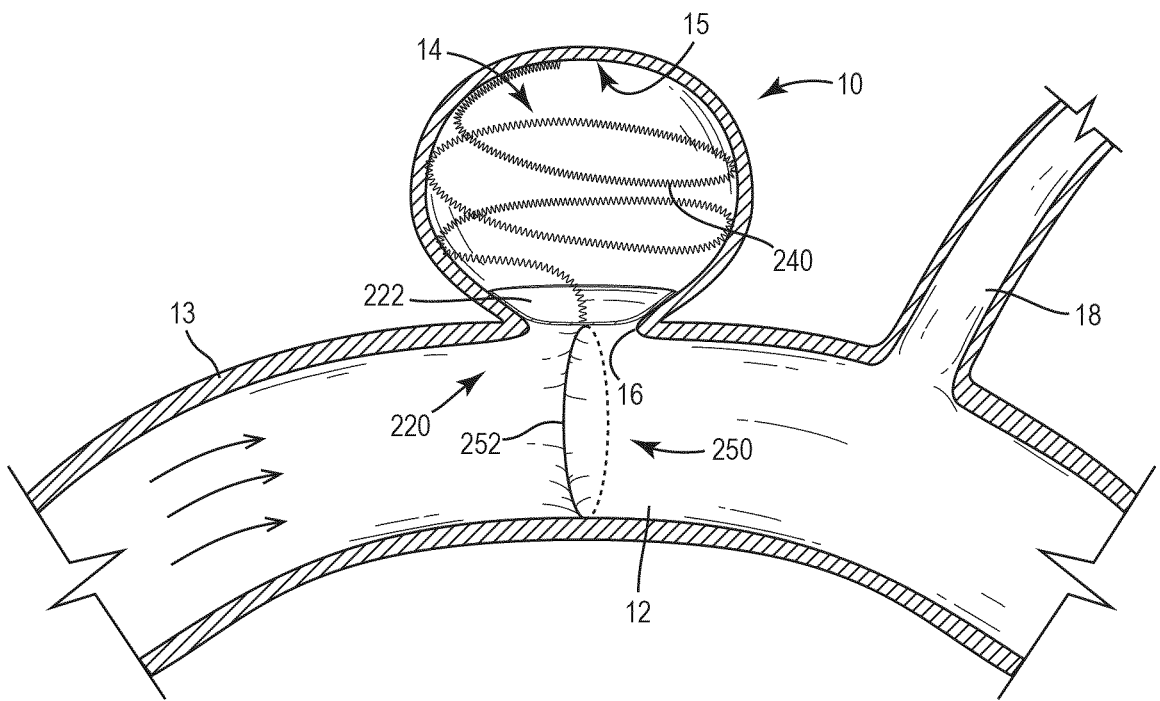
FIG. 7 is a schematic cross-section side view of an aneurysm with an endovascular device configured to occlude the aneurysm, according to another exemplary embodiment.

Referring to FIG. 7, according to an exemplary embodiment, the outer anchoring member 250 includes a loop 252 of a coil formed from a suitable biocompatible metal or alloy (e.g., platinum, stainless steel, nickel-titanium alloy, etc.). The metal coil may be similar to the coils that are typically utilized in an endovascular coiling procedure. The loops 252 is coupled to the inner cover 222 and contacts the wall 13 of the blood vessel 12 in one embodiment. The loop 252 is oriented perpendicular to the flow of blood through the blood vessel 12 in one embodiment. Multiple coils or loops 252 can be utilized in one embodiment.

Figure 8:
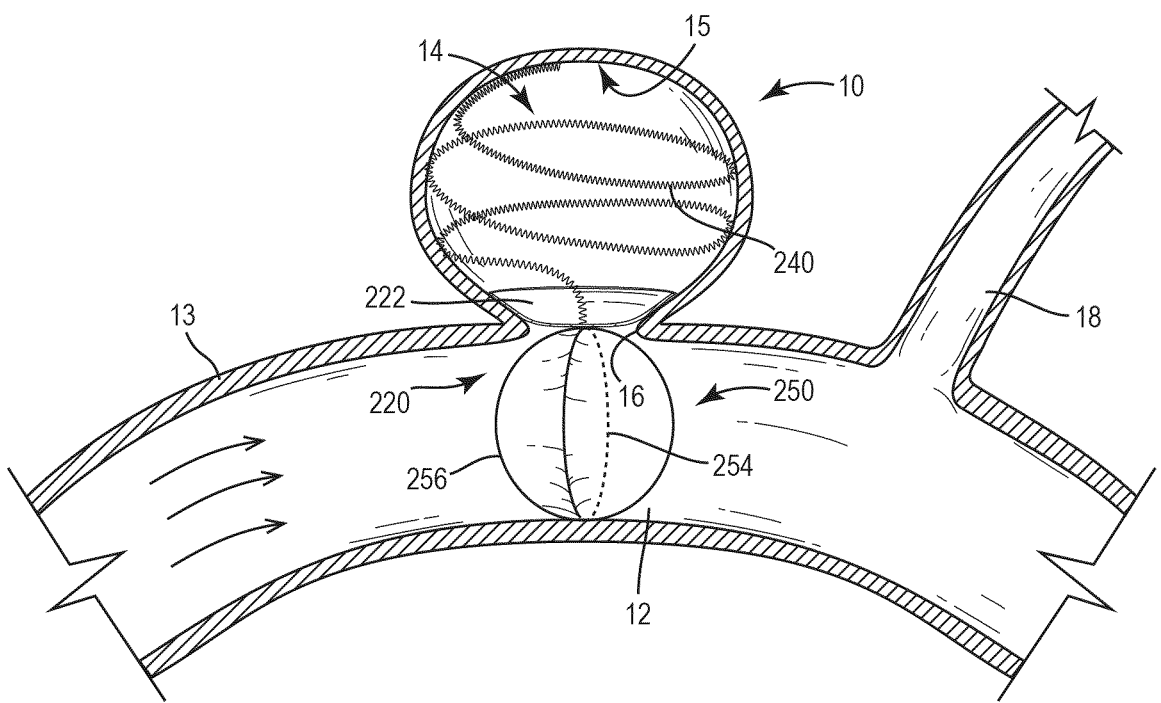
FIG. 8 is a schematic cross-section side view of an aneurysm with an endovascular device configured to occlude the aneurysm, according to another exemplary embodiment.

Referring to FIG. 8, according to an exemplary embodiment, the outer anchoring member 250 includes a first loop 254 and a second loop 256. The loops 254 and 256 may be loops of a coil formed from a suitable biocompatible metal or alloy (e.g., platinum, stainless steel, nickel-titanium alloy, etc.). At least one of the loops 254 and 256 are coupled to the inner cover 222 and contact the wall 13 of the blood vessel 12. The first loop 254 extends about the inner circumference of the blood vessel 12 such that it is oriented perpendicular to the flow of blood through the blood vessel 12. The second loop 256 is oriented parallel to the flow of blood through the blood vessel 12. The second loop 256 is formed of a coil having a fairly small diameter and does not substantially impede the flow of blood through the blood vessel. In other embodiment, the outer anchoring member 250 may include more than two loops. The orientation, number, and size of the loops may vary depending on the size and shape of the blood vessel 12.

Figure 9:
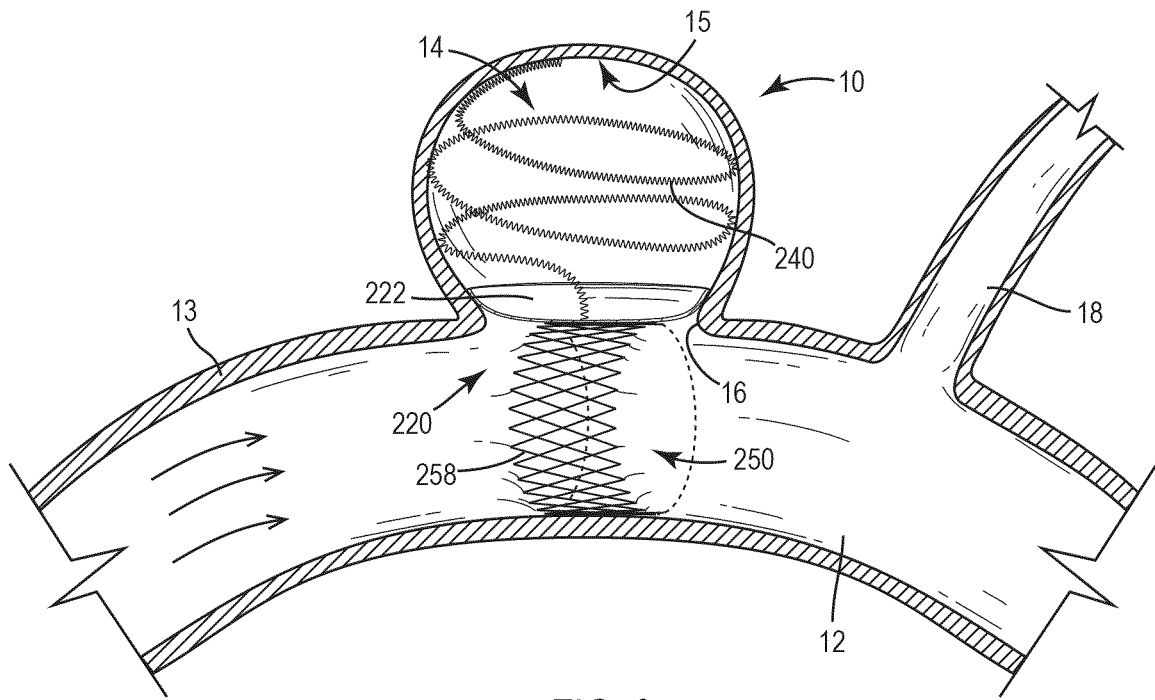
FIG. 9 is a schematic cross-section side view of an aneurysm with an endovascular device configured to occlude the aneurysm, according to another exemplary embodiment.

Referring to FIG. 9, according to another exemplary embodiment, the outer anchoring member 250 includes a stent 258 formed from a suitable biocompatible metal or alloy (e.g., platinum, stainless steel, nickel-titanium alloy, etc.) or a suitable biocompatible polymer. The stent 258 is introduced in a collapsed state to the blood vessel 12 proximate the aneurysm 10 via the catheter 30. Once deployed into the blood vessel 12, the stent 258 is expanded to compress against the walls of the blood vessel 12. The stent 258 may be self-expandable or may be expanded with another device, such as an inflatable balloon. All or part of the stent 258 may be coated or covered with a radiopaque material, such as a platinum to allow for visualization of the stent 258 (e.g., during and after the placement of the stent 258).

The stent 258 is not intended to occlude the neck portion 16 of the aneurysm 10, but instead forms a structure to facilitate the placement and anchoring of the inner cover 222. The stent 258 therefore does not need to be as wide as or wider than the neck portion 16, but may be a relatively short body (e.g., shorter than the width of the neck portion 16 of the aneurysm 10). The relatively short length of the stent 258 reduces the likelihood that the outer anchoring member 250 will disrupt surrounding bodies, such as a side branch 18 of the blood vessel 12. Further, the stent 258 may have a non-dense, relatively open configuration with variable cell morphology which may extend proximally in the blood vessel 12 from the neck portion 16. In other embodiments, the stent 258 may be a solid member, such as a band formed of a metal or alloy with a relatively thin thickness.

In another embodiment, the outer anchoring member 250 may be a temporary member that is removed with the catheter 30 after the occlusion device 320 has been placed in the neck portion 16 of the aneurysm and has been coupled to the walls of the aneurysm 10. For example, the outer anchoring member may be a balloon that is inflated in the blood vessel 12 proximate the aneurysm to provide a temporary structure to support the inner cover 222.

Figure 10:
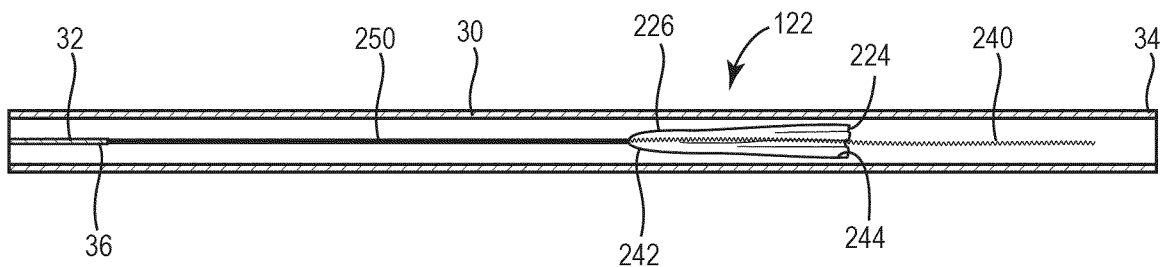
FIG. 10 is a schematic cross-section view of the occlusion device of FIG. 7 inside of a catheter, according to an exemplary embodiment.

Referring now to FIG. 10, the inner cover 222, the inner anchoring member 240, and the outer anchoring member 250 are shown disposed within a catheter 30 according to an exemplary embodiment. The outer anchoring member 250 is coupled to a distal end 36 of the push wire 32 and is housed, in a collapsed configuration, within the lumen of the catheter 30. The outer anchoring member 250 is coupled to the inner cover 222, which is housed, in a collapsed configuration, within the lumen of the catheter 30 upstream of the outer anchoring member 250. The outer anchoring member 250 may be coupled to the inner cover 222, for example, with an adhesive. In the collapsed configuration, a peripheral portion 224 of the inner cover 222 is upstream of a central portion 226 to which the outer anchoring member 250 is coupled on a first surface 244. The inner anchoring member 240 is coupled to a second surface 246 of the inner cover 222 opposite the first surface 242 and is disposed within the lumen of the catheter 30 upstream of the inner cover 222.

The occlusion device 220 including the inner cover 222 and the inner anchoring member 230 is deployed within the aneurysm 20 similar to the process described above with reference to FIGS. 3A-3E. With the distal end 34 of the catheter 30 positioned proximate to the neck portion 26 of the aneurysm 20, the push wire 32 is moved within the lumen relative to the catheter 30. The inner anchoring member 240 is pushed out of the catheter and into the internal volume 24, where is contacts the interior surface 25 of the aneurysm 20. The push wire 32 is moved further until the inner cover 222 begins to emerge from the end 34 of the catheter 30 to expand into an expanded configuration within the internal volume 24. The catheter 30 and/or the push wire 32 is then retracted until the inner cover 222 is seated against the interior surface 25 of the aneurysm 20 and held in place by the inner anchoring member 240. The push wire 32 is moved further until the outer anchoring member 250 emerges from the catheter 30. The outer anchoring member 250 may be, for example, one or more loops 252, 254, or 256, or the stent 258. The distal end 36 of the push wire 32 is detached from the outer anchoring member such that the catheter 30 and the push wire 32 may be withdrawn from the blood vessel 22 while the inner cover 22 remains in the neck portion 26 of the aneurysm 20 with the inner anchoring member 240 coupled to the second surface 246 and the outer anchoring member 250 disposed in the blood vessel 12. In other embodiments, the push wire 32 may be coupled directly to the inner cover 222 and the outer anchoring member 250 may be deployed separately (e.g., from another catheter).

Referring now to FIG. 11-14, an occlusion device 320 is shown according to an exemplary embodiment disposed in the neck portion 16 of the aneurysm 10 to disrupt or halt the flow of blood flow between the vessel 12 and the internal volume 14 of the aneurysm, thereby reducing the likelihood that the aneurysm 10 will rupture. The occlusion device 320 is configured to be low profile device, minimizing disruptions to surrounding bodies, such as a side branch 18 of the blood vessel 12. The occlusion device 320 may be configured to be biodegradable or bioabsorbable material and may be configured to promote endothelialization.

The occlusion device 320 includes an inner cover 322 (e.g., plate, membrane, etc.) disposed within the internal volume 14 of the aneurysm 10 and similar to the inner cover 32 described above. The occlusion device 320 further includes an outer cover 360 disposed in the blood vessel 12 proximate the aneurysm 10. The outer cover 360 may be coupled to the inner cover 322 provides a relatively rigid body to support the inner cover. The outer cover 360 reduces the likelihood that the inner cover 322 will be displaced from the neck portion 34 by the fluid pressure of the blood in the blood vessel 32. The outer cover 360 may be utilized instead of or in addition to other devices, such as the inner anchoring member 140 or the outer anchoring member 250 to secure the inner cover 322 in the neck portion 16.

Figure 11:
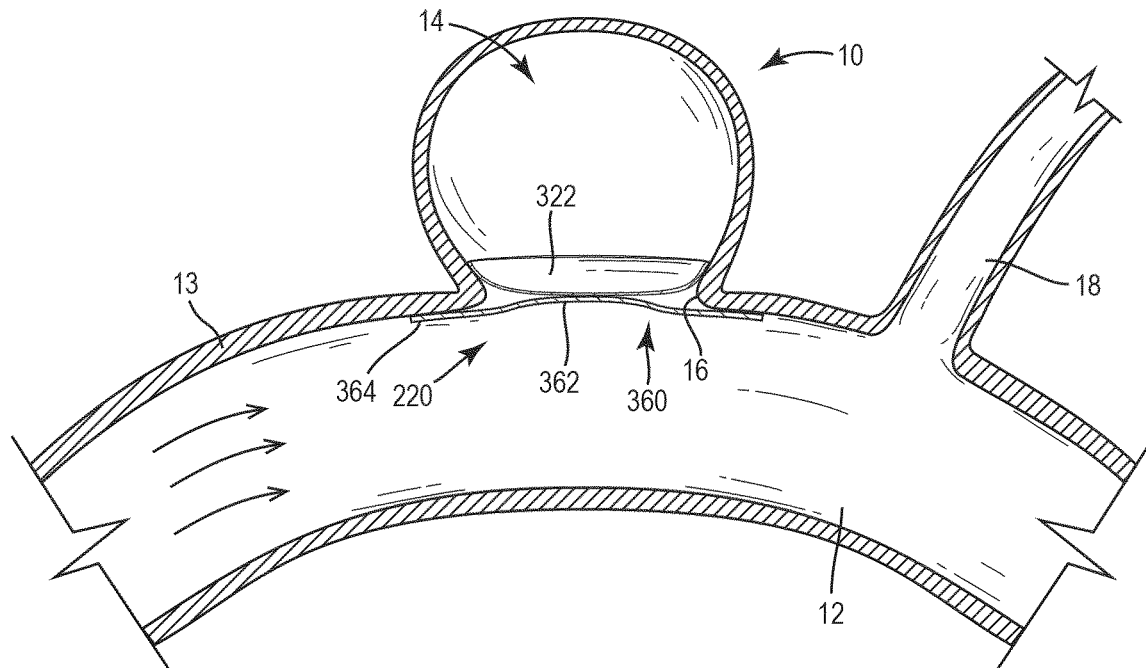
FIG. 11 is a schematic cross-section side view of an aneurysm with an endovascular device configured to occlude the aneurysm, according to another exemplary embodiment.

Referring to FIG. 11, according to an exemplary embodiment, the outer cover 360 is a relatively thin member (e.g., plate, sheet, etc.) formed from a suitable biocompatible such as a metal or alloy (e.g., platinum, stainless steel, nickel-titanium alloy, etc.), or a polymer (e.g., PTFE, etc.). According to an exemplary embodiment, the outer cover 360 has a thickness of less than 2 mm. According to a preferred embodiment, the outer cover has 360 has a thickness of less than 1 mm. The outer cover 360 is a low-profile body that does not substantially impede the flow of blood through the blood vessel 12. The outer cover 360 includes a peripheral portion 362 that contacts the wall 13 of the blood vessel 12 around the neck portion 16 of the aneurysm 10 and a central portion 364 disposed in the neck portion 16. The central portion 364 may be integrally formed with the inner cover 322 or may be coupled to the inner cover 322 (e.g., with a suitable adhesive). All or part of the outer cover 360 may be coated or covered with a radiopaque material, such as a platinum, to allow for visualization of the outer cover 360 (e.g., during and after the placement of the outer cover 360). In embodiment, outer cover 360 is attached to inner cover at a center area having less area than the neck portion 16 (e.g., 90 percent, 75 percent, or 50 percent of the area of the neck portion). In one embodiment, the center area has a circular shape.

Figure 12:
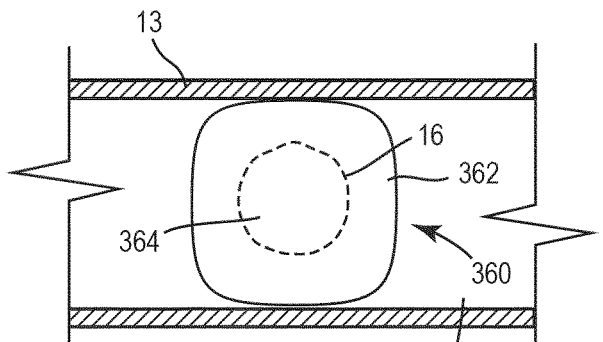
FIG. 12 is a schematic cross-sectional bottom view of an aneurysm occlusion device, according to an exemplary embodiment.

The outer cover 360 is not intended to occlude the neck portion 16 of the aneurysm 10, but instead forms a structure to facilitate anchor the inner cover 322. The outer cover 360 therefore does not need to completely cover the neck portion 16. The outer cover 360 may therefore be shaped such that portions of the neck portion 160 are uncovered and/or may be formed of a porous material (e.g., a mesh). Referring to FIG. 12, in one embodiment, the outer cover 360 may be a sheet that completely covers the neck portion 16 such that the peripheral portion 362 of the outer cover 360 extends about the entirety of the neck portion 16.

Figure 13:
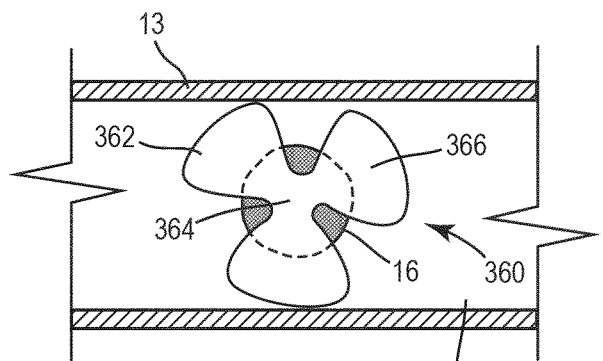
FIG. 13 is a schematic cross-sectional bottom view of an aneurysm occlusion device, according to an exemplary embodiment.

Referring to FIG. 13, in another embodiment, the outer cover 360 may include multiple segments or sections such as radial lobes 366 that extend outward from the neck portion 16. Each of the lobes 366 may include a central portion 364 disposed within the neck portion 16 and a peripheral portion 364 extending beyond the neck portion 16 to contact the wall 13 of the blood vessel 12.

Figure 14:
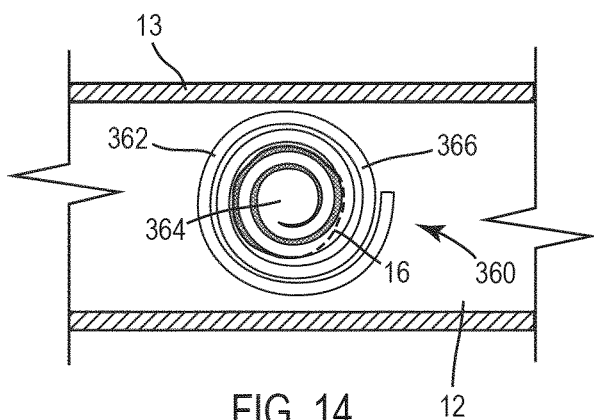
FIG. 14 is a schematic cross-sectional bottom view of an aneurysm occlusion device, according to an exemplary embodiment.

Referring to FIG. 14, in another embodiment, the outer cover 360 may include a spiral body 368. The inner loops of the spiral body 368 may form the central portion 364 while the outer loops of the spiral body 368 may form the peripheral portion 362.

The outer cover 360 may be deployed from a catheter in the same procedure as the inner cover 322. The outer cover 360 may therefore be configured to be collapsible such that it can be coupled to the inner cover 322 and housed within the catheter. The outer cover 360 may be configured such that, within the catheter, the central portion 364 is coupled to the inner cover 322 and positioned upstream of the peripheral portion 362. The inner cover 322 may be deployed as described with reference to FIGS. 3A-D. Once the inner cover 322 is deployed from the catheter and positioned in the neck portion 16, the push wire of the catheter may be advanced further to deploy the outer cover 360. The fluid pressure of the blood within the blood vessel 12 forces the outer cover 360 against the wall 13 of the blood vessel 12. In other embodiments, the push wire 32 may be coupled directly to the inner cover 322 and the outer cover 360 may be deployed separately (e.g., from another catheter).

Figure 15:
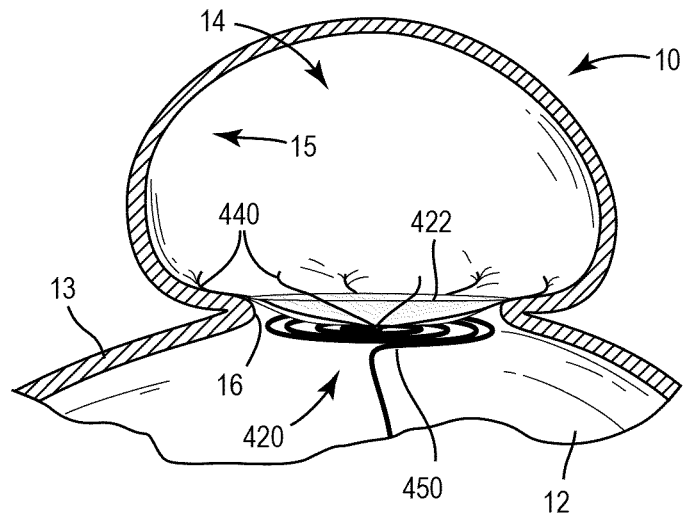
FIG. 15 is a schematic cross-sectional side view of an aneurysm with an endovascular device configured to occlude the aneurysm, according to another exemplary embodiment.
Figure 16:
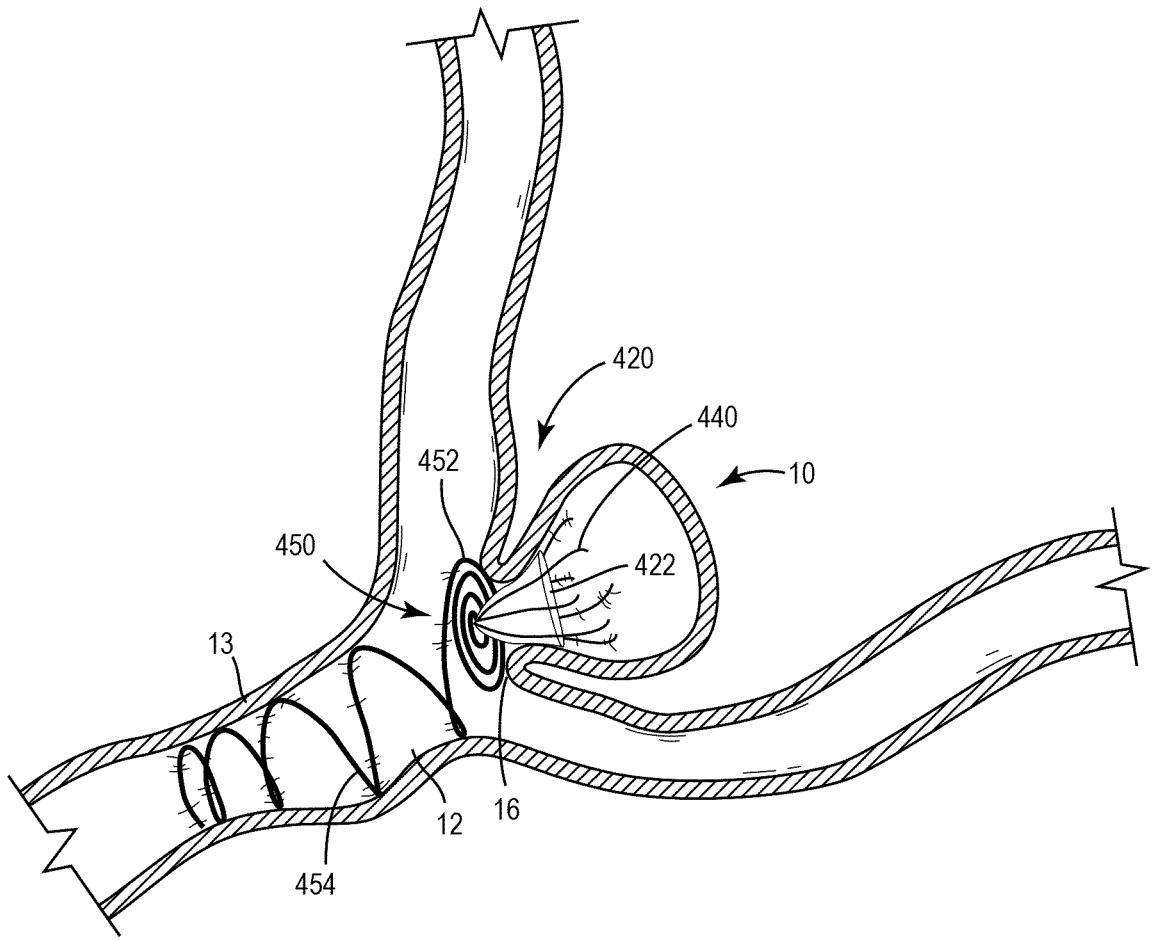
FIG. 16 is a schematic cross-sectional side view of an aneurysm with an endovascular device configured to occlude the aneurysm, according to another exemplary embodiment.

Referring now to FIG. 15-16, an occlusion device 420 is shown according to an exemplary embodiment disposed in the neck portion 16 of the aneurysm 10. The occlusion device 420 includes an inner cover 422 (e.g., plate, membrane, etc.) disposed within the internal volume 14 of the aneurysm 10. The occlusion device 420 further includes an inner anchoring member 440 disposed within the aneurysm 10 and/or an outer anchoring member 450. The inner anchoring member 440 is configured to anchor the inner cover 422 within the aneurysm 10 in the neck portion 16. According to an exemplary embodiment, the inner anchoring member 440 includes one or more struts or arms formed from a suitable biocompatible metal or alloy (e.g., platinum, stainless steel, nickel-titanium alloy, etc.). The inner anchoring member 440 is coupled to the inner cover 122 and is configured to extend beyond the periphery of the inner cover 422 to contacts the interior surface 15 of the aneurysm 10. The inner anchoring member 140 may therefore be used to facilitate the positioning of the inner cover 422 in an aneurysm 10 having a relatively wide neck 16. The struts or arms of the inner anchoring member 140 do not fill the entire internal volume 14 or a substantial portion of the internal volume 14. The "mass effect" of the aneurysm 10 is reduced, as the size of the aneurysm 10 is allowed to shrink as the vessel heals, thereby reducing the pressure placed on the surrounding tissue by the aneurysm. The orientation, number, and length of the arms of the inner anchoring member 440 may vary depending on the size and shape of the aneurysm 10. The arms of the inner anchoring member 440 may be configured to collapse together to be delivered via a microcatheter, similar to the microcatheter 30 described above.

Referring still to FIGS. 15-16, the outer anchoring member 450 includes first portion 452 (e.g., distal portion) disposed at the neck 16 and coupled to the inner cover 420 and a second portion 454 (e.g., proximal portion) disposed in the vessel 12. The outer anchoring member 450 is formed from a suitable biocompatible metal or alloy (e.g., platinum, stainless steel, nickel-titanium alloy, etc.) or a suitable biocompatible polymer. All or part of the outer anchoring member 450 may be coated or covered with a radiopaque material, such as a platinum to allow for visualization of the outer anchoring member 450 (e.g., during and after the placement of the outer anchoring member 450). The outer anchoring member 450 is introduced in a collapsed (e.g., straightened) state to the blood vessel 12 proximate the aneurysm 10 via a catheter. Once deployed into the blood vessel 12, the outer anchoring member 450 expands such that at least a portion of the outer anchoring member compresses against the walls of the blood vessel 12. The outer anchoring member 450 may be formed as a single, continuous spiral, with loops of the spiral being formed to have variable properties (e.g., diameter, thickness, flexibility, etc.). For example, the first portion 452 may be formed to have relatively small diameter, flexible coils while the second portion 454 may be formed to have larger, relatively rigid coils providing an increased outward radial force to facilitate positioning the outer anchoring member 450 along the wall 13 of the blood vessel 12.

Figure 17:
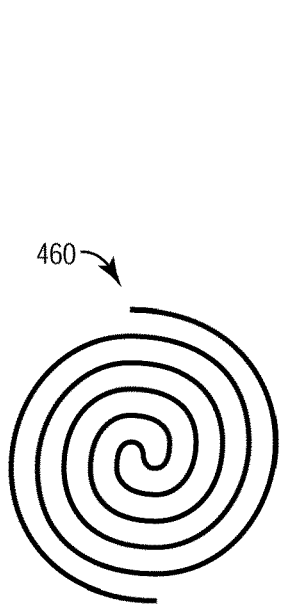
FIG. 17 is a schematic bottom view of an outer anchoring member for an aneurysm occlusion device, according to an exemplary embodiment.

Referring to FIG. 17, according to another exemplary embodiment, a portion of an outer anchoring member 460 may be formed as a dual spiral. According to other exemplary embodiments, the outer anchoring member may be formed as a wide variety of other shapes (e.g., web-shaped, star-shaped, etc.) to provide a desired flexibility and support for the inner cover at the neck of the aneurysm.

Figure 18A:
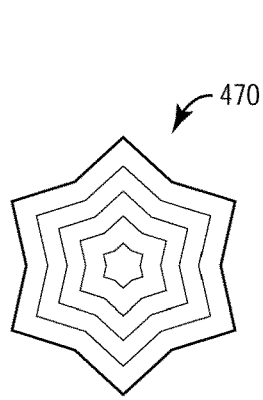
FIG. 18A is a schematic top view of a cover for an aneurysm occlusion device, according to an exemplary embodiment.
Figure 18B:
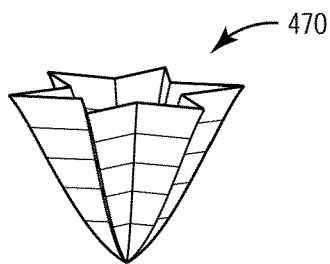
FIG. 18B is a schematic side view of the cover of FIG. 18A in a partially folded configuration.

Referring to FIGS. 18A-18B, according to another exemplary embodiment, an inner cover 470 for an occlusion device may be a star-shaped body. The inner cover 470 may be formed (e.g., creased, scored, molded) to fold and collapse along predefined fold lines.

Figure 19:
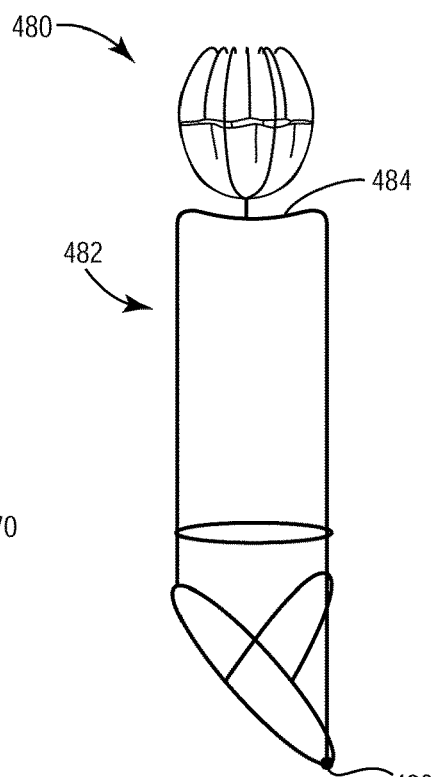
FIG. 19 is a schematic side view of an endovascular device configured to occlude an aneurysm, according to another exemplary embodiment.

Referring now to FIG. 19, an occlusion device 480 is shown having an outer anchoring member 482. The outer anchoring member 482 is a recapturable body that may be variously shaped (e.g., straight, spiral, multi-spiraled, coven, etc.). The outer anchoring member 482 is formed as a relatively open structure having a minimal number of segments that form a framework that is capable of positioning and securing the occlusion device 480 while minimizing contact with the walls of the blood vessel. The open nature of the outer anchoring member 482 has a low risk of jailing a branch blood vessel or otherwise altering the flow of blood through the blood vessel.

Figure 20:
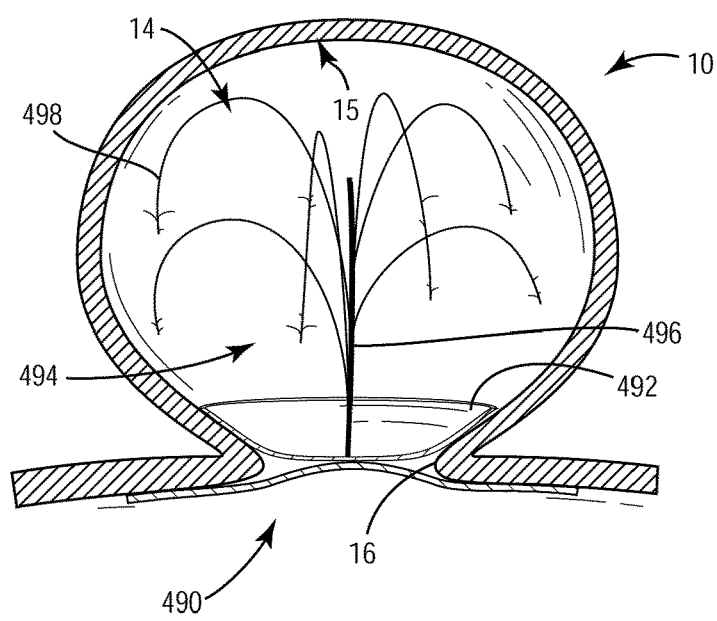
FIG. 20 is a schematic cross-sectional side view of an aneurysm with an endovascular device configured to occlude the aneurysm, according to another exemplary embodiment.

Referring to FIG. 20, an inner anchoring member 494 for an occlusion device 490 is shown according to another exemplary embodiment. The inner anchoring member 494 includes a central wire 496 coupled to the cover 492 and one or more outer wires 498 coupled to the central wire 496. The outer wires 498 extend outward from the central wire 496 to contact the interior surface 15 of the aneurysm 10. The inner anchoring member 494 is introduced in a collapsed (e.g., straightened) state to the aneurysm 10 via the catheter 30. Once deployed into the aneurysm 10, the catheter 30 is withdrawn, allowing the outer wires 498 to expand outward such that at least a portion of the outer wires 298 contact the inner surface 15 to position and anchor the cover 492 in the neck 16.

The construction and arrangement of the elements of the aneurysm occlusion device as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited herein. For example, elements shown as integrally formed may be constructed of multiple parts or elements, the position of elements may be reversed or otherwise varied, and the nature or number of discrete elements or positions may be altered or varied. It should be noted that the elements and/or assemblies of the system may be constructed from any of a wide variety of materials that provide sufficient strength, durability, or biocompatibility. Other substitutions, modifications, changes and omissions may be made in the design, operating conditions and arrangement of the preferred and other exemplary embodiments and medical procedures without departing from the scope of the present invention.

What is claimed is:

1. An apparatus for treating an aneurysm in a blood vessel, the apparatus comprising:
   an elongate push member configured to be advanced within a lumen of a catheter; and
   an occlusion element detachably disposed on a distal portion of the push member, the occlusion element comprising:
      a single inner anchoring member, wherein the push member extends from a proximal side of the inner cover and the single inner anchoring member extends from a distal side of the inner cover, wherein the occlusion element is configured to fit within the lumen of the catheter and is configured to be slid out of the lumen at the distal end of the catheter in response to movement of the push member relative to the catheter, wherein the inner cover has a collapsed configuration for placement through the lumen of the catheter and an expanded configuration when advanced out of the lumen of the catheter, wherein in the expanded configuration, a distally-facing surface of the inner cover comprises a concavity and a peripheral portion of the inner cover has an expanded diameter, such that when the occlusion element is delivered into an aneurysm having a neck portion and an interior surface, the expanded diameter of the inner cover is greater than a diameter of the neck portion of the aneurysm, such that a first portion of a proximally-facing surface of the inner cover contacts a first portion of the interior surface of the aneurysm and such that a second portion of the proximally-facing surface of the inner cover covers the neck portion of the aneurysm, and wherein the single inner anchoring member comprises a single loop configured to contact a second portion of the interior surface of the aneurysm.

2. The apparatus of claim 1, wherein the inner cover has a closed umbrella-like shape in its collapsed configuration and an open umbrella-like shape in its expanded configuration.

3. The apparatus of claim 1, wherein the inner cover comprises a mesh formed by a plurality of fibers.

4. The apparatus of claim 1, wherein the single inner anchoring member is a coil.

5. The apparatus of claim 1, wherein the single inner anchoring member has a flexibility such that it can be coiled within the aneurysm.

6. The apparatus of claim 1, wherein the second portion of the interior surface of the aneurysm is opposite the neck portion of the aneurysm.

7. The apparatus of claim 1, further comprising:
   an outer anchoring member coupled to the inner cover, the outer anchoring member configured to be disposed within a blood vessel proximate the aneurysm and on a blood vessel side of the neck portion of the aneurysm, wherein at least a portion of the outer anchoring member contacts an interior surface of the blood vessel.

8. The apparatus of claim 7, wherein the outer anchoring member comprises at least one radial lobe extending out from the inner cover to engage with the interior surface of the blood vessel.

9. The apparatus of claim 1, wherein the occlusion element is configured to slide off the push member after expanding.

10. The apparatus of claim 1, further comprising a cutting element disposed to cut the push member.

11. The apparatus of claim 1, further comprising a stent configured to support the inner cover.

12. The apparatus of claim 11, wherein the stent is configured to compress against the inner wall of a blood vessel proximate the aneurysm.

13. The apparatus of claim 11, wherein the stent is self-expandable.

14. The apparatus of claim 11, wherein the stent is configured to facilitate anchoring of the inner cover.

15. The apparatus of claim 1, wherein the inner cover comprises a star-shaped body.

16. The apparatus of claim 1, wherein the inner cover comprises a membrane.

17. The apparatus of claim 1, wherein the push member comprises a wire.

18. The apparatus of claim 1, wherein the single inner anchoring member has a variable stiffness.

19. The apparatus of claim 1, wherein the occlusion element has a closed position and an open position, and is biased toward the open position.

20. The apparatus of claim 1, wherein the single inner anchoring member extends from the concavity of the inner cover.

* * * * *

UNITED STATES PATENT AND TRADEMARK OFFICE
CERTIFICATE OF CORRECTION

PATENT NO. : 11,883,032 B2
APPLICATION NO. : 17/112229
DATED : January 30, 2024
INVENTOR(S) : Aamir Badruddin et al.

It is certified that error appears in the above-identified patent and that said Letters Patent is hereby corrected as shown below:

In the Claims

Column 13, Claim 1, Line 8: insert -- an inner cover; and -- before "a single inner anchoring member, wherein"

Signed and Sealed this
Ninth Day of April, 2024

Katherine Kelly Vidal
*Director of the United States Patent and Trademark Office*